(12) United States Patent
Dickrell, III et al.

(10) Patent No.: US 9,836,667 B2
(45) Date of Patent: Dec. 5, 2017

(54) SYSTEM AND METHOD FOR ANALYZING RANDOM PATTERNS

(71) Applicant: University of Florida Research Foundation, Inc., Gainesville, FL (US)

(72) Inventors: Daniel John Dickrell, III, Gainesville, FL (US); Wallace Gregory Sawyer, Gainesville, FL (US); Richard D. Clark, III, Gainesville, FL (US)

(73) Assignee: UNIVERSITY OF FLORIDA RESEARCH FOUNDATION, INC., Gainesville, FL (US)

( * ) Notice: Subject to any disclaimer, the term of this patent is extended or adjusted under 35 U.S.C. 154(b) by 1 day.

(21) Appl. No.: 14/351,414

(22) PCT Filed: Apr. 11, 2013

(86) PCT No.: PCT/US2013/036167
§ 371 (c)(1),
(2) Date: Apr. 11, 2014

(87) PCT Pub. No.: WO2013/155301
PCT Pub. Date: Oct. 17, 2013

(65) Prior Publication Data
US 2015/0254524 A1   Sep. 10, 2015

Related U.S. Application Data

(60) Provisional application No. 61/622,636, filed on Apr. 11, 2012.

(51) Int. Cl.
*A61B 3/12* (2006.01)
*G06K 9/52* (2006.01)
(Continued)

(52) U.S. Cl.
CPC .............. *G06K 9/52* (2013.01); *A61B 3/1233* (2013.01); *A61B 5/0261* (2013.01);
(Continued)

(58) Field of Classification Search
CPC . G06T 2207/30104; G06T 2207/30101; G06T 2207/30188; G06T 2211/404;
(Continued)

(56) References Cited

U.S. PATENT DOCUMENTS 7,668,351 B1   2/2010   Soliz et al.
8,090,164 B2   1/2012   Bullitt
(Continued)

FOREIGN PATENT DOCUMENTS

EP   0923955 B1   6/1999
JP   2007209589 A   8/2007
(Continued)

OTHER PUBLICATIONS

Pivkin, I. V., P. D. Richardson, D. H. Laidlaw, and G. E. Karniadakis. "Combined effects of pulsatile flow and dynamic curvature on wall shear stress in a coronary artery bifurcation model." Journal of biomechanics 38, No. 6 (2005): 1283-1290.*
(Continued)

*Primary Examiner* — Sumati Lefkowitz
*Assistant Examiner* — Carol Wang
(74) *Attorney, Agent, or Firm* — Cantor Colburn LLP

(57) ABSTRACT

Disclosed herein is a system and a method for analyzing apparent random pathways, patterns, networks, or a series of events and characterizing these apparent random pathways, patterns, networks, or a series of events by constructal analysis. The resulting statistical values obtained can be used to compare the apparent random pathways, patterns, networks, or a series of events with other apparent random pathways, patterns, networks, or a series of events. The
(Continued)

Network flow calculation using resistive fluid elements comparison can yield knowledge about the apparent random pathways, patterns, networks, or a series of events as well as the neighborhood or surroundings of the apparent random pathways, patterns, networks, or a series of events.

21 Claims, 13 Drawing Sheets

(51) Int. Cl.
| | |
|---|---|
| *G06T 7/00* | (2017.01) |
| *A61B 5/026* | (2006.01) |
| *G06K 9/62* | (2006.01) |
| *A61B 6/00* | (2006.01) |
| *A61B 8/00* | (2006.01) |
| *A61B 5/02* | (2006.01) |

(52) U.S. Cl.
CPC .......... *G06K 9/6212* (2013.01); *G06T 7/0012* (2013.01); *A61B 5/02007* (2013.01); *A61B 6/501* (2013.01); *A61B 8/00* (2013.01); *A61B 2576/00* (2013.01); *G06T 2207/10032* (2013.01); *G06T 2207/10072* (2013.01); *G06T 2207/10116* (2013.01); *G06T 2207/10132* (2013.01); *G06T 2207/30041* (2013.01); *G06T 2207/30101* (2013.01); *G06T 2207/30188* (2013.01)

(58) Field of Classification Search
CPC ........ A61B 2017/1107; A61B 5/02007; A61B 6/504; A61B 2576/00; A61B 2034/107; A61B 3/1233; A61B 8/0891
See application file for complete search history.

(56) References Cited

U.S. PATENT DOCUMENTS

| | | | |
|---|---|---|---|
| 8,428,317 | B2 | 4/2013 | Kimia |
| 8,734,357 | B2 | 5/2014 | Taylor |
| 2003/0166999 | A1* | 9/2003 | Liu .......... G01R 33/56 600/410 |
| 2005/0122477 | A1 | 6/2005 | Alster et al. |
| 2006/0235669 | A1* | 10/2006 | Charbel ............ G06F 19/321 703/11 |
| 2008/0027356 | A1* | 1/2008 | Chen .............. G06T 7/0012 600/587 |
| 2008/0159604 | A1 | 7/2008 | Wang et al. |
| 2009/0101271 | A1 | 4/2009 | Ishida |
| 2009/0177098 | A1 | 7/2009 | Yakubo et al. |
| 2009/0270738 | A1 | 10/2009 | Izatt et al. |
| 2009/0328239 | A1 | 12/2009 | Brauner |
| 2010/0061601 | A1 | 3/2010 | Abramoff et al. |
| 2010/0172554 | A1 | 7/2010 | Kassab et al. |
| 2010/0234678 | A1 | 9/2010 | Pryor et al. |
| 2010/0240117 | A1 | 9/2010 | Ying |
| 2010/0296709 | A1* | 11/2010 | Ostrovsky-Berman ........... G06T 7/0081 382/128 |
| 2010/0299077 | A1* | 11/2010 | Kassab ........... A61B 5/02007 702/19 |
| 2011/0026789 | A1 | 2/2011 | Hsu et al. |
| 2011/0046764 | A1 | 2/2011 | Kan |
| 2012/0162438 | A1* | 6/2012 | Thakor ............ A61B 5/0062 348/161 |
| 2012/0203530 | A1* | 8/2012 | Sharma ........... G06F 19/3437 703/9 |
| 2013/0226003 | A1* | 8/2013 | Edic ............. A61B 5/026 600/454 |

FOREIGN PATENT DOCUMENTS

| | | |
|---|---|---|
| JP | 2011086054 A | 4/2011 |
| RU | 2319448 C2 | 3/2008 |

OTHER PUBLICATIONS

Zhao, Fei, and Rahul Bhotika. "Coronary artery tree tracking with robust junction detection in 3D CT angiography." In Biomedical Imaging: From Nano to Macro, 2011 IEEE International Symposium on, pp. 2066-2071. IEEE, 2011.*
Riley, James D., Bruce L. Rhoads, Daniel R. Parsons, and Kevin K. Johnson. "Influence of junction angle on three-dimensional flow structure and bed morphology at confluent meander bends during different hydrological conditions." Earth Surface Processes and Landforms 40, No. 2 (2015): 252-271.*
Johnson, Michael J., and Geoff Dougherty. "Robust measures of three-dimensional vascular tortuosity based on the minimum curvature of approximating polynomial spline fits to the vessel midline." Medical engineering & physics 29, No. 6 (2007): 677-690.*
Pawel Topa (2011). Network Systems Modelled by Complex Cellular Automata Paradigm, Cellular Automata—Simplicity Behind Complexity, Dr. Alejandro Salcido (Ed.), ISBN: 978-953-307-230-2, InTech, Available from: http://www.intechopen.com/books/cellular-automata-simplicity-behind-complexity/network-systems-modelledby-complex-cellular-automata-paradig.*
Wechsatol, W., S. Lorente, and A. Bejan. "Optimal tree-shaped networks for fluid flow in a disc-shaped body." International Journal of Heat and Mass Transfer 45, No. 25 (2002): 4911-4924.*
Bejan, A., and S. Lorente. "The constructal law and the thermodynamics of flow systems with configuration." International journal of heat and mass transfer 47, No. 14 (2004): 3203-3214.*
Bejan, Adrian, and James H. Marden. "The constructal unification of biological and geophysical design." Physics of Life Reviews 6, No. 2 (2009): 85-102.*
Azegrouz, Hind, et al. "Thickness dependent tortuosity estimation for retinal blood vessels." Engineering in Medicine and Biology Society, 2006. EMBS'06. 28th Annual International Conference of the IEEE. IEEE, 2006. 4675-4678.
European Search Report for EP Application No. 13775875.1; dated Feb. 18, 2016 (9 pages).
International Preliminary Report on Patentability for International Application No. PCT/US2014/033801 International Filing Date Apr. 11, 2014; dated Oct. 13, 2015; (5 pages).
International Preliminary Report on Patentability for International Application No. PCT/US2013/036167 International Filing Date Apr. 11, 2013; dated Aug. 11, 2014; (20 pages).
International Search Report for International Application No. PCT/US2014/033801 International Filing Date Apr. 11, 2014; dated Aug. 6, 2014; (5 pages).
Rengier et al. "3D printing based on imaging data: review of medical applications" International Journal of Computer Assisted Radiology and Surgery Jul. 2010, vol. 5, Issue 4, pp. 335-341.
Written Opinion for International Application No. PCT/US2014/033801 International Filing Date Apr. 11, 2014; dated Aug. 6, 2014; (4 pages).
Bejan, Adrian et al. "Constructal theory of generation of configuration in nature and engineering" Journal of Applied Physics, vol. 100, Issue 4 (2006) pp. 041301-1-041301-27.
International Search Report for PCT/US2013/036167 International Filing Date Apr. 11, 2013; dated Jul. 29, 2013; (5 pages).
Barry R. Masters "Fractal Analysis of the Vascular Tree in the Human Retina" Annual Review of Biomedical Engineering, vol. 6, Aug. 2004; pp. 427-452.
Wang, Li et al. "Analysis of Retinal Vasculature Using a Multiresolution Hermite Model" IEEE Transactions on Medical Imaging, vol. 26, No. 2, Feb. 2007 pp. 137-152.
Written Opinion for International Application No. PCT/US2013/036167 International Filing Date Apr. 11, 2013; dated Jul. 29, 2013; (6 pages).
Extended European Search Report for EP Application No. 14783006.1; dated Nov. 21, 2016 (9 pages).

* cited by examiner

Example of retinal digital image

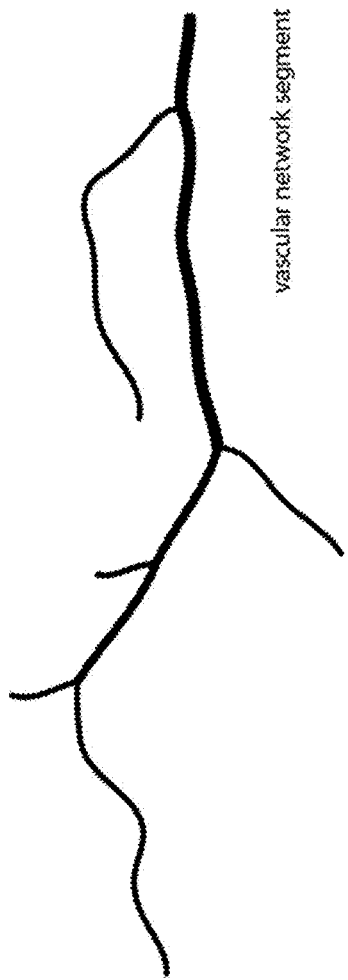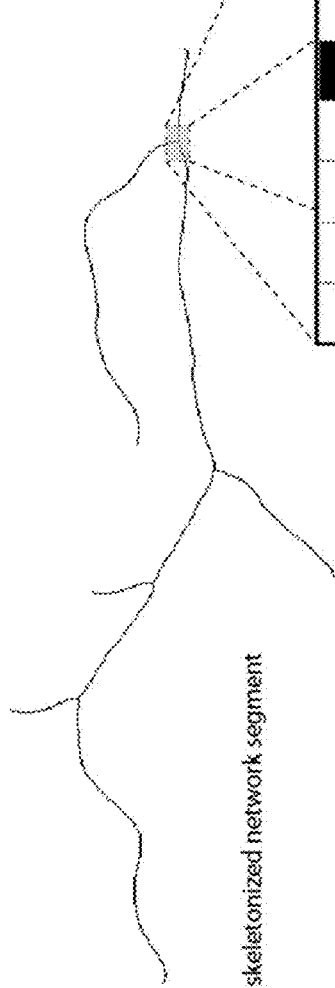
Figure 3

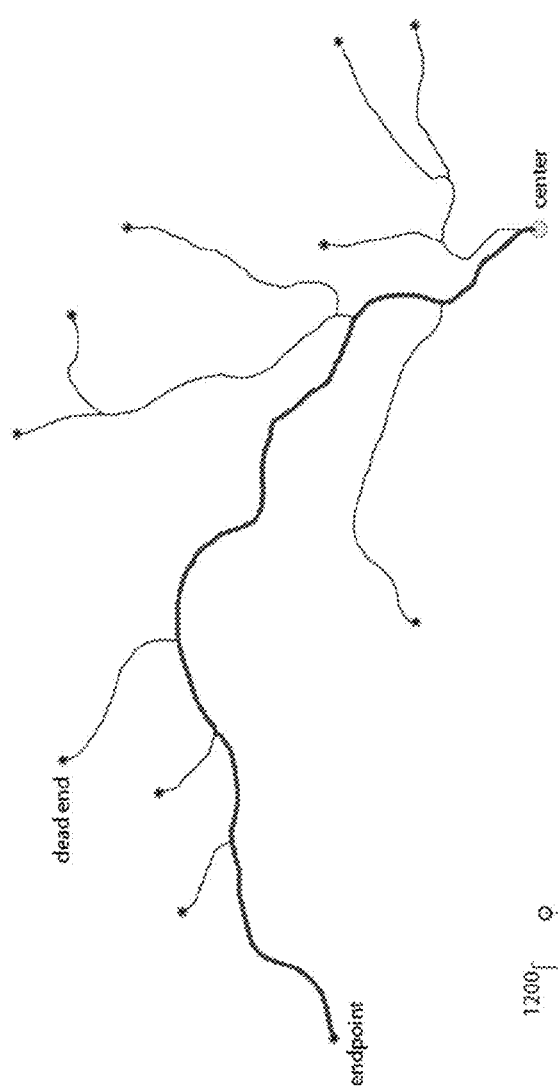
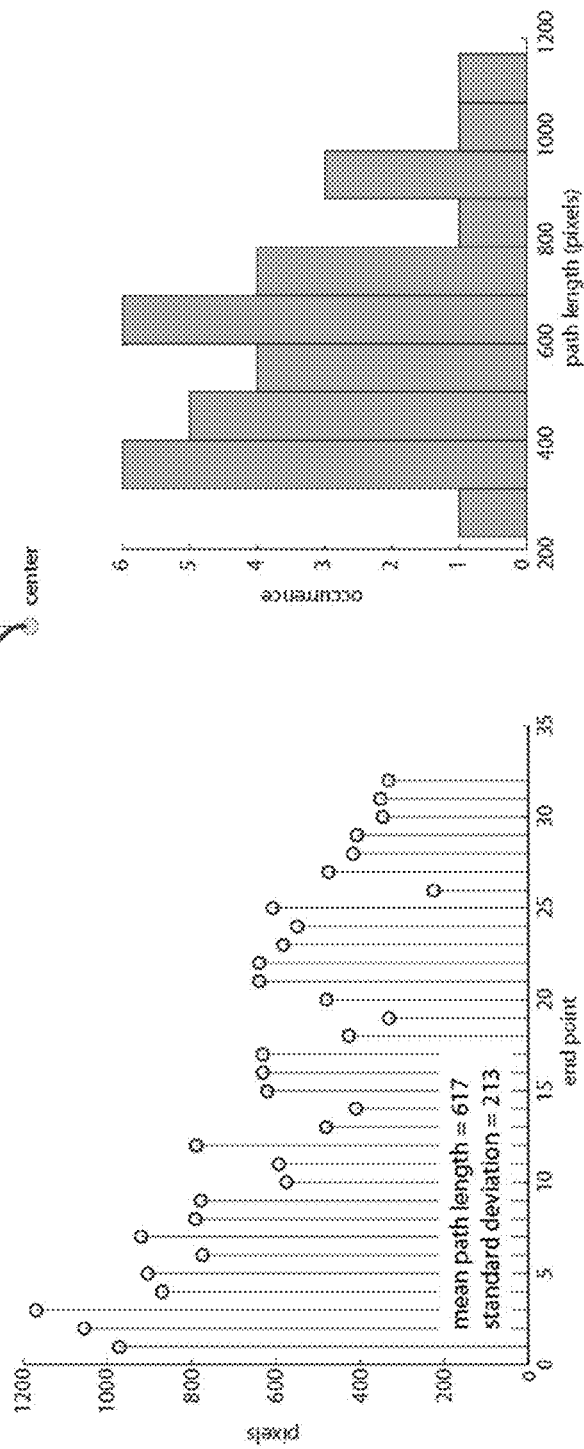
Figure 6

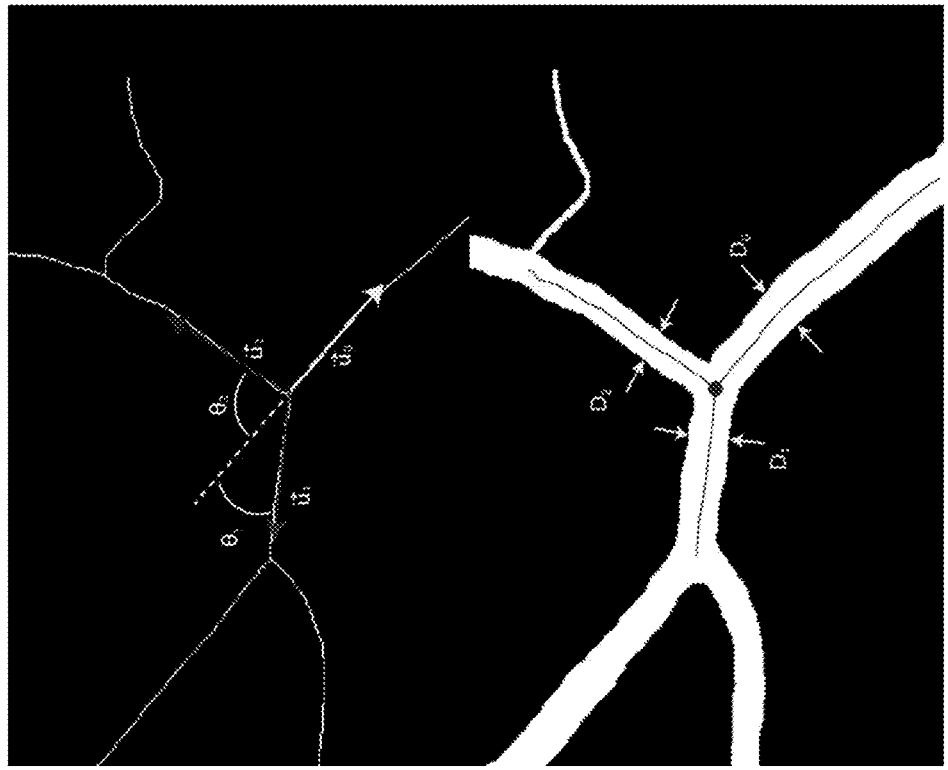
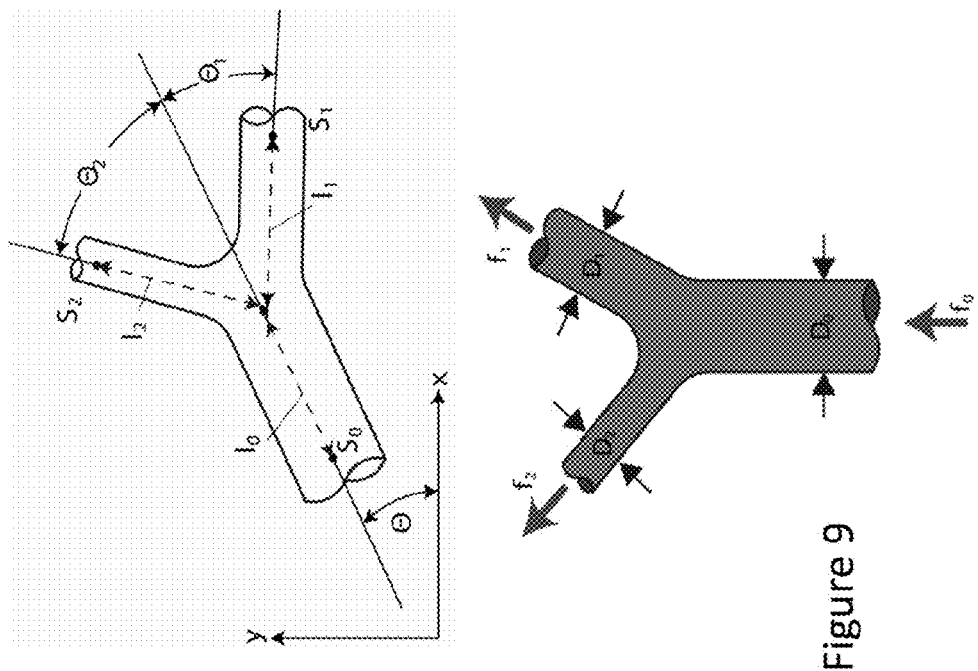
Figure 9
Vessel branching angles and vessel diameter ratios governing the "optimal" vascular network shape Network flow calculation using resistive fluid elements Volumetric flow results of imaged network Flow velocity results of imaged network

SYSTEM AND METHOD FOR ANALYZING RANDOM PATTERNS

CROSS-REFERENCE TO RELATED APPLICATIONS

This application claims priority to International Application PCT/US13/36167 filed Apr. 11, 2013 which claims priority to U.S. Provisional Application No. 61/622,636, filed on Apr. 11, 2012, the entire contents of which are hereby incorporated by reference.

BACKGROUND

This disclosure relates to systems and to methods for analyzing objects that contain a flow field and whose features appear to develop randomly. It relates to systems and to methods for measuring apparent random patterns and pathways in structures that contain flow fields. In particular, this disclosure relates to systems and to methods for imaging and analyzing apparent random patterns and pathways that are contained in a biological system, where the pattern and pathway contains a flow field.

Seemingly or apparent random patterns and pathways are often a part of systems and objects that occur naturally and that generally contain a flow field. An example of a naturally occurring random pathway is a river that travels across the landscape. The river possesses several bends and tributaries and it is often difficult to predict which section of the river will contain a bend or a tributary. Another example of a naturally occurring random pathway is the path taken by blood vessels in the eyeball, the heart, the lungs, the brains, or other parts of a living being. Blood vessels have a number of branches and it is difficult to predict where these branches will occur, the number of branches and the average orientation of these branches that a particular part (e.g., the heart, the eyeball, and the like) of a particular living being will have. A tree is another example of a naturally occurring structure whose branches take random pathways and the point of contact of one branch with another is an apparently random event. All of the aforementioned examples—the river, the blood vessels and the tree contain flow fields.

The ability to determine and to measure the structure of such apparently random objects permits predictive capabilities for the design of future objects. It also permits a comparison of one set of the objects (that are grown or developed under one set of circumstances) with another set of equivalent objects (that are grown or developed under a second set of circumstances). It is therefore desirable to develop methods that can be used to measure the structures and to quantify their features so that they can be compared with one another and to predict the behavior of future objects.

SUMMARY

Disclosed herein is a system for performing a constructal analysis, the system comprising a processor and a memory to perform a method comprising initiating capture of an image of a subject; where the subject comprises an apparent random pathway, pattern, or network; where the apparent random pathway, pattern or network comprises a flow field; initiating at least one image processing algorithm on the image; identifying at least one apparent random pathway, pattern, network, or one series of events in the image; identifying a center and at least one endpoint associated with the at least one apparent random pathway, pattern, network, or the event in the image; calculating a path length associated with the at least one apparent random pathway, pattern, network, or the event in the image; calculating at least one statistical measure associated the at least one apparent random pathway, pattern, network, or the one series of events in the image; where the statistical measure is calculated by constructal analysis; and correlating the at least one statistical measure with a plurality of respective other statistical measures of at least one other apparent random pathway, pattern, network, or the one series of events in the subject or in another subject.

Disclosed herein too is a method for performing a constructal analysis of a apparent random pathway, pattern, network, or a series of events, comprising capturing at least one image of the apparent random pathway, pattern, network, or a series of events; where the apparent random pathway, pattern or network comprises a flow field; initiating at least one image processing algorithm on the at least one image; identifying in at least one computing device, at least one apparent random pathway, pattern, network, or event of the apparent random pathway, pattern, network, or the series of events; identifying a center and at least one endpoint associated with the at least one apparent random pathway, pattern, network, or event, each of the at least one apparent random pathway, pattern, network, or event originating from the center of the apparent random pathway, pattern, network, or the series of events; calculating, in the at least one computing device, a tortuosity measure associated with each of the at least one apparent random pathway, pattern, network, or event; calculating, in the at least one computing device, at least one statistical measure associated with the apparent random pathway, pattern, network, or the series of events; and correlating the at least one statistical measure with a plurality of respective other statistical measures of at least one other apparent random pathway, pattern, network, or the series of events.

Disclosed herein too is a method for performing a constructal analysis of a subject biological system, comprising the steps of capturing at least one image of the subject biological system; initiating, in at least one computing device, at least one image processing algorithm on the at least one image; identifying at least one blood vessel in a vascular network of the subject biological system; identifying, in the at least one computing device, a plurality of junction angles associated with the at least one blood vessel in the vascular network of the subject biological system; calculating, in the at least one computing device, an optical flow measure associated with each of the at least one junction angle; calculating, in the at least one computing device, at least one statistical measure associated with a plurality of optimal flow angles associated with the subject biological system; and code that correlates the at least one statistical measure with a plurality of respective other statistical measures of at least one other patient.

BRIEF DESCRIPTION OF THE DRAWINGS

FIGS. 3 and 4 are drawings illustrating a binary representation of a portion of a vascular network according to various embodiments of the present disclosure;

FIG. 6 illustrates one method of obtaining a path length associated with the various paths of a vascular network according to various embodiments of the present disclosure;

FIG. 9 illustrates an example of a constructal analysis of a subject retina according to various embodiments of the present disclosure;

DETAILED DESCRIPTION

Figure 1:
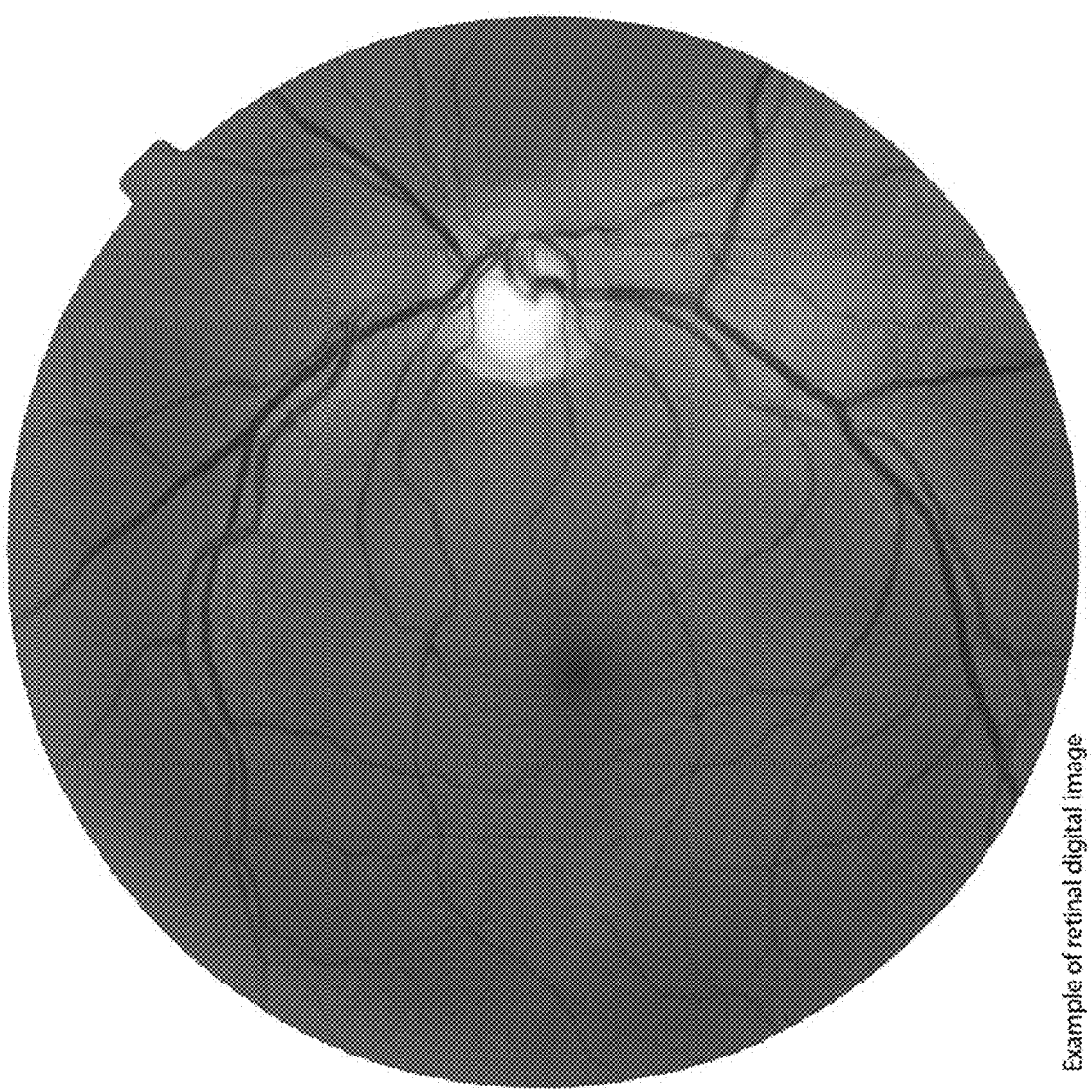
FIG. 1 is a drawing of an image of a subject retina according to various embodiments of the present disclosure.

Disclosed herein is a system that can be used to analyze images of objects that contain an apparently a random pattern or network that contains a flow field. The system can measure the apparently random pattern, pathway, or network and be used to characterize its features such as its end to end distance, its radius of gyration, its tortuosity, the ability of the structure to permit a fluid, atomic and sub-atomic particles (e.g., electrons, protons, photons, holes, and the like), energy, and the like, to flow through it. In one exemplary embodiment, features of the random pattern, pathway, or network can be characterized using constructal analysis so long as it involves a flow along the apparently random pattern, pathway, or network. The system disclosed herein can also be used to deduce information about the neighborhood surrounding the apparently random patterns, pathways, and networks. It can also be used to study the events surrounding a series of events so long as the series of events are affected by the event.

The term "seemingly" or "apparent" or "apparently" is used because the pathways, patterns or networks described herein appear to be random (i.e., they have tortuous pathways that appear to be random), but can actually be characterized using thermodynamic concepts such as the "efficiency of the system" "boundary conditions", "energy minimization", "guiding forces", "design constraints", "minimization of losses" or the like. The apparent pathway, pattern or network may also be characterized as a naturally occurring pathway, pattern or network and comprises a flow field. It can also be called a transport network since it transports a fluid, atomic and sub-atomic particles, energy, or the like.

The resulting analysis and the data obtained therefrom can be used to compare a first random pattern, pathway, network, or a series of events with a second random pattern, pathway, network, or a series of events that is grown or developed under different circumstances, or at another location, or at another time in the same or different location. The comparison can be used to assess the quality of the first random pattern, pathway, network, or a series of events with respect to the second random pattern, pathway, network, or series of events. The resulting analysis, the data obtained therefrom and any data pertaining to the comparison can be transmitted to a screen, printed out on a sheet, saved and stored on a solid state drive, a hard disc drive or a floppy disc.

The system comprises an imaging device in operative communication with a computer that contains code or software to analyze a portion of the image and to provide various parameters that characterize the pathway, pattern, network, or random series of events. The code or software comprises an image processing algorithm that can measure one or more features of the image and can provide details about an analyzed feature of the image using constructal analysis.

Disclosed herein too is a method that can be used to analyze images of objects that contain a random pattern, pathway, network, or series of events. The method comprises capturing an image of a random pathway, pattern, network, or a series of events, or the like. The image is then transmitted to a computer (e.g., a device having a memory and a processor) where an algorithm is initiated to generate parameters of the image using constructal analysis. The generation of parameters is undertaken by identifying at least one random pathway, pattern, network, or a series of events from a plurality of random pathways, patterns, networks, or a series of events contained in the image. The at least one random pathway is then characterized by measuring at least one of its end to end distance, its radius of gyration, its junction angles associated with another part of the random pathway, vessel widths, vessel lengths, vessel tortuosities, junction exponents, asymmetry ratios, area ratios, parent-child angle changes, parent-child vessel diameter ratios-child-child diameter ratios, overall links/volume of observable vasculature, metrics as a function of vessel generations, metrics as a function of location, and the like.

The aforementioned parameters can then be used to develop an estimate of an optical flow measure associated with the apparently random pathway, pattern, or network. The aforementioned parameters can be used to calculate volumetric flow rates, flow velocities, pressure gradients, shear stress and shear strain rates, energy requirements, fluid resistance/conductance, and the like. The aforementioned parameters can also be used to estimate a statistical measure associated with a plurality of parameters for the entire apparently random pathway, pattern, network, or a series of events. The statistical measures can be used to compare the apparently random pathway, pattern, network, or a series of events with another apparently random pathway, pattern, network, or a series of events.

Determining performance efficiency (of the apparently random pathway, pattern or network) versus an "ideal" constructally optimized design can be used to judge performance improvement or deterioration. Deterioration of the pathway, pattern or network can occur due to disease, treatment, intervention, adjustments, and the like.

The system and the method described herein are advantageous in that they can be used to assess the health of a system of blood vessels present in a living being. The blood vessels can be present in the eyeball, the heart, the brain, the lungs, and the like of a living being. The living being can be a human being, an animal, a bird or a fish. The statistical measures derived from this constructal analysis can be used to assess the health of the blood vessels and may also be used to diagnose or to pinpoint diseases that a particular living being is suffering from. The system and the method described herein can also be used to assess the health of a system of flow channels present in vegetation, the health of chemical pipelines in the chemical industry or in other transport systems, the migratory patterns of various species or birds and animals, the transportation of water into the subterranean layers of the earth, and the like. It can be deployed wherever there is a flux of a species from one point in a system to another point in the system.

The system and method described herein will now be detailed with respect to a plurality of blood vessels present in the retina of a living being. The efficient and orderly transport of energy and material within (and between) systems of living beings is desirable for the proper functioning of those systems. Biophysical flow systems or systems that move quantities such as heat, blood, air, or other materials within the body of a living being naturally evolve from birth to death into characteristic shapes. The structure of these systems can be imaged and mapped using various medical imaging technologies. Using this image data, the patient health physiology or pathology state can be quantified numerically by employing the governing physical laws of efficient, naturally-evolved flow transport (also referred to as constructal theory or constructal laws). In other words, a constructal analysis of a system can be performed to assess whether its properties correlate to healthy or unhealthy baselines.

Various systems within the body, such as, an eye, brain, heart, lungs, nerves, kidney, breast, or any other system in which the flow of biological materials occurs, can be imaged, and the flow of materials through the system can be correlated with conditions that are observed in other healthy patients and/or patients having a diagnoses or one or more conditions. The examples presented herein relate to the examination of blood flow through the vascular network visible in the image of a retina. However, the concepts, systems and methods disclosed herein can be employed in various organs, vascular networks and/or systems or networks that can be imaged in some way within the body of a living being. The concepts, systems and methods can also be used to characterize and to compare other apparently random pathways, patterns, networks, or a series of events that lie outside the body of a living being or occur outside the body of a living being.

In one embodiment of the disclosure, quantitative measures corresponding to the vascular network visible in imagery of a retina can be calculated which can be correlated to existing or potential eye disease of the vascular network or other conditions to which certain calculated measures can be correlated. In one embodiment, geometric calculations of the structure of the vascular network visible in the retina to detect one or more specific ophthalmologic pathology. Additionally, recommendations of one or more retinal vascular network health conditions can be generated.

Figure 2:
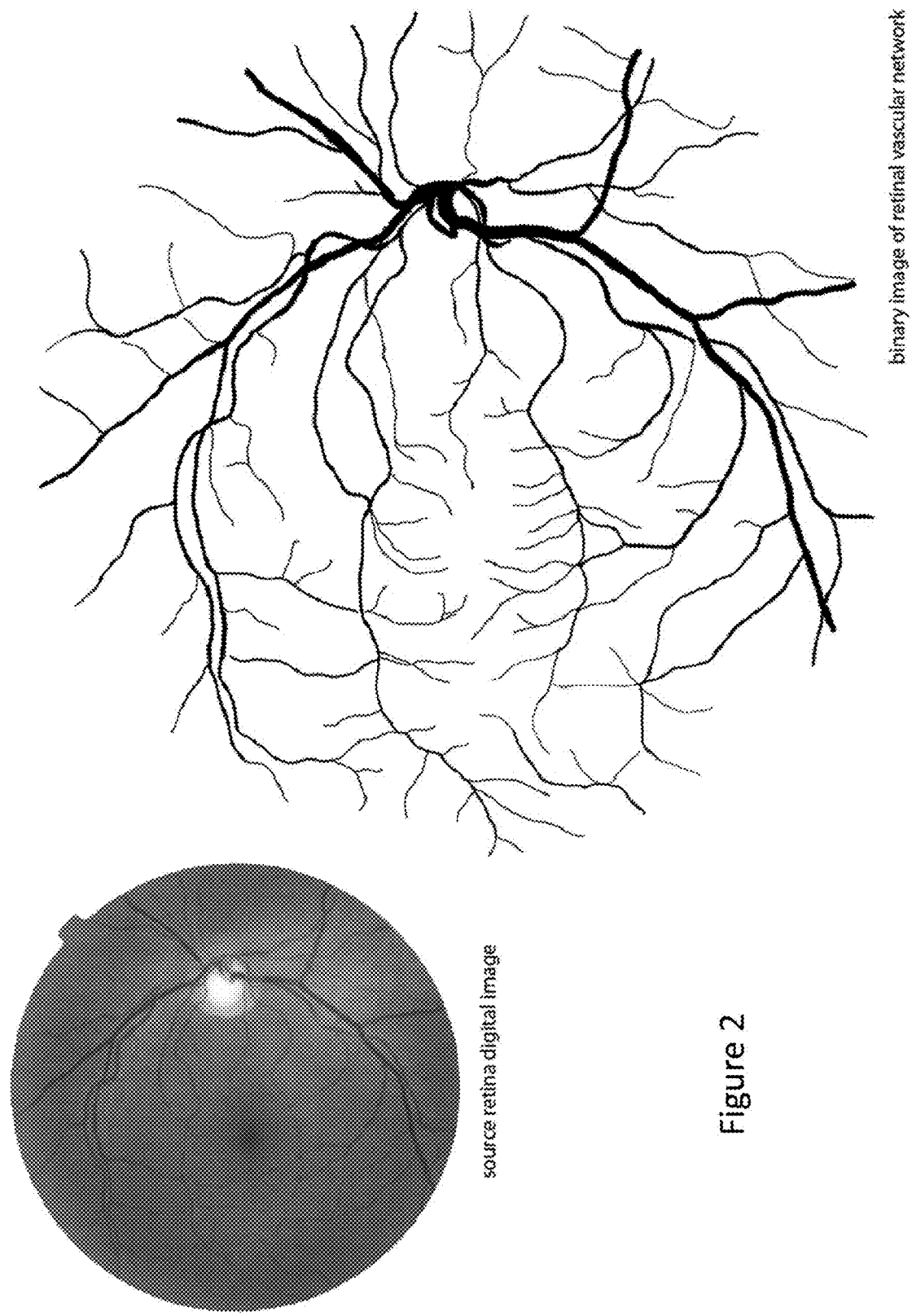
FIG. 2 is a drawing of a vascular network that can be identified in an image of a subject retina according to various embodiments of the present disclosure.

In one embodiment, an image of a retina can be captured by various types of image capture devices and/or methods. For example, various types of medical imaging technologies can be employed, such as photography, magnetic resonance imaging (MRI), OCT, CT, ultrasound, ultrasound thermography, positron emission tomography, opto-acoustics, and other imaging techniques as can be appreciated to capture image of a biological system. FIG. 1 is photograph of an image of a subject retina, while the FIG. 2 is an image of a vascular network that can be identified in an image of a subject retina.

Various filtering, thresholding, image recognition and/or feature recognition techniques (e.g., biometric systems) can be employed to isolate "segment" the vascular network that is represented in a captured image of a retina. Accordingly, upon isolation of the vascularization and/or vascular structure of a retina, the vascular structure can be transformed into binary image or representation that can express its structure in a binary form. It is to be noted that other imaging systems can be used for the imaging of non-vascular systems. Apparently random pathways, patterns, networks, or a series of events may also be captured by other visual image capturing systems (e.g., visible light cameras, infra-red cameras) or by audio recording equipment (e.g., ultrasound imaging, magnetic recording media, and the like), installed in satellites, aircraft, observation towers, cellphones, or the like.

In one embodiment, upon isolation of the exemplary vascular network of the retina by employing one or more image processing techniques that are referenced above, a binary skeleton can be created that represents the paths taken by blood vessels in the vascular structure of the retina. FIG. 3 illustrates one example of a binary skeleton that can be generated by express these paths. Upon creation of such a binary representation of the vascular structure of the retina, embodiments of the disclosure can employ one or more calculations and/or algorithms to assess the condition of the eye and/or health of a subject. In one embodiment, the binary representation of the vascular structure of a retina can include a two dimensional array data structure that expresses the position of the vascular structure of the retina.

Figure 4:
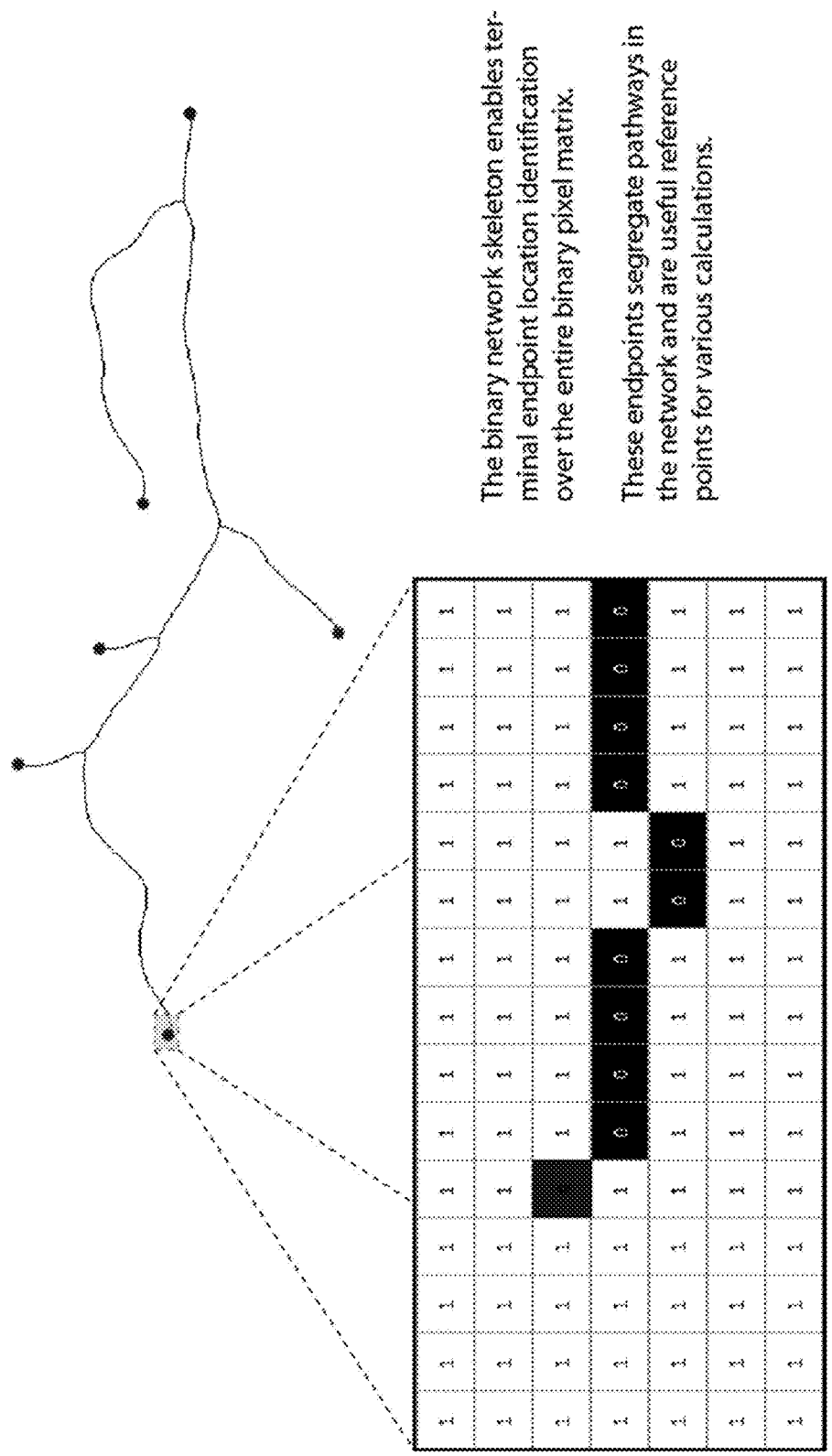

In another embodiment, as shown in FIG. 4, the binary structure can include a binary pixel matrix where the location of vascular structure is represented by '0' entries, and the absence of vascular structure is represented by '1' entries. It should be appreciated that these values can be transposed and that any other alternative structure can be used to digitally represent the vascular structure of a retina after the retina is isolated using the image processing techniques referenced above.

The constructal analysis method can be detailed as follows. The processing of the image begins by obtaining a binary image of an isolated arterial or venous network. The image is a pixelated image with white pixels being equivalent to the vasculature and dark pixels representing the background. A determination is made of the total number of particles (discrete areas of white pixels) and other pixels (i.e. all particles) but the one comprising of the most pixels are removed. In other words, the imaged vasculature is smoothed out to a series of points that represent the highest pixel density along the path of the vasculature. A thinning algorithm is then used that reduces the network to paths with widths of one pixel. Any "spurs" or small lengths of network containing endpoints are then removed. A flow source (i.e., a series of interconnected arteries or veins through which flow occurs) in the image is then used for further study by manually selecting a suitable area in the image as follows.

Manually select the left and right edges of the optic disc to determine a pixel-to-micron ratio based on a diameter of 1.76 mm. Determine all endpoints and junctions in the network by analyzing each vascular pixel's connectivity to neighboring pixels. Define the network by "walking" along the vascular network from each junction. The following are determined:

Nodes—junctions, endpoints, or the flow source area.
Segments—lengths of pixels connecting nodes The width of all segments in the vascular network in the optical disc are determined by performing a principal component analysis on the thinned segment, then taking N perpendicular measurements along the segment in the binary image and averaging the measurements. N is generally between 3 and 7. Determine the lengths of segments by accumulating and summing up pixel-to-pixel lengths from one end of a segment to the other. To pixels sharing a side of the segment add a length of 1.0 while for pixels sharing a corner of the segment, add a length of 1.41 multiplied by the length of the side of the pixel.

Determine the generation of each segment by attributing a generation number of "1" to each segment connected to the flow source. Each bifurcation thereafter adds a generational number to the child segments. For example, a child segment that branches of a main segment is given the number 1, while a $2^{nd}$ child segment that branches of the $1^{st}$ child segment is given the number 2, and so on. Determine the viscosity in each segment based on its diameter and an assumed hematocrit level. The haematocrit (Ht or HCT), also known as packed cell volume (PCV) or erythrocyte volume fraction (EVF), is the volume percentage (%) of red blood cells in blood. It is normally about 45% for men and 40% for women. It is considered an integral part of a person's complete blood count results, along with hemoglobin concentration, white blood cell count, and platelet count. Determine the fluid conductance in each segment using the Hagen-Poiseuille equation.

In short, as detailed above, after isolating a portion of a binarized vascular system (or an equivalent flow system such as a river, and the like), extraneous rough edges and small segment lengths are removed. Segment widths and lengths are calculated and each generational segment is assigned a numerical value depending upon its location from the main segment. The viscosity of fluids being transported through the segments is then computed. The flow in each segment and in the entire binarized vascular system is then determined using the Hagen-Poiseuille equation.

$$\Delta P = \frac{8\mu L Q}{\pi r^4} \quad (1)$$

where $\Delta P$ is the pressure loss through the segment; L is the length of segment; $\mu$ is the dynamic viscosity; Q is the volumetric flow rate through the segment; and r is the radius of the segment.

For each segment endpoint, determine a virtual bifurcating network whose relative diameter is a function of Murray's Law and relative length is a function of data found in the literature. Murray's law, or Murray's principle is a formula for relating the radii of child segments to the radii of the parent segment of a lumen-based system. The branches classically refer to the branching of the circulatory system or the respiratory system, but have been shown to also hold true for the branching of xylem, the water transport system in plants.

Murray's analysis facilitates a determination of the segment radius that minimizes expenditure of energy by the organism. Larger vessels lower the energy expended in pumping fluid (e.g. blood, water, and the like) because the pressure drop in the vessels reduces with increasing diameter according to the Hagen-Poiseuille equation. Larger vessels increase the overall volume of fluid flowing through the system. In the event, that the system is a vascular system (i.e., one that transports blood), increasing the flow of blood means increasing metabolic support. Murray's law helps balance these factors.

For n child segments arising from a common parent segment, the formula is:

$$r_p^3 = r_{c1}^3 + r_{c2}^3 + r_{c3}^3 + \ldots r_{cn}^3$$

where $r_p$ is the radius of the parent segment, and $r_{c1}$, $r_{c2}$, $r_{c3}$, and $r_{cn}$ are the radii of the respective child branches. From Murray's law, it may be seen that larger diameter tubes are heavier because of both the tubing and the additional volume of enclosed fluid, but the pressure losses incurred are reduced and so the mass of the pumping system that is used can be lower. The (inner) tube diameter $d_i$ which minimizes the total mass (tube+fluid+pump), is given by the following equation in laminar flow:

$$d_i^6 = \frac{1024\mu Q^2}{\pi^2 K[\rho TUBE(C^2 + C) + \rho FLUID]}$$

where Q is the volume flow rate, $\mu$ is the fluid viscosity, K is the power-to-weight ratio of the pump, $\rho$TUBE is the density of the tubing material, c is a constant of proportionality linking vessel wall thickness with internal diameter and the $\rho$FLUID is the density of the fluid.

For turbulent flow the equivalent relation is $$d_i^7 = \frac{80 Q^3 f \rho FLUID}{\pi^3 K[\rho TUBE(C^2 + C) + \rho FLUID]}$$

where f is the Darcy friction factor. The junction relations above can therefore be applied in the following form in turbulent flow:

$$r_p^{7/3} = r_{c1}^{7/3} + r_{c2}^{7/3} + r_{c3}^{7/3} + \ldots + r_{cn}^{7/3}$$

The binary image of the network is bifurcated down to approximately segments having diameters of approximately 5.0 micrometers. A conductance is calculated for each virtual network (binarized image) by using serial/parallel relationships for the different virtual segments. The conductances for parallel segments are added while the reciprocal of conductances for serial segments are added to produce an equivalent conductance. This method is used on the entire vascular network to determine a total equivalent conductance. If a pressure is assigned to the source node and a pressure assigned to the capillary level, a series of linear equations can be used to determine the flow rate and pressure at every segment and junction. If the flow rates and pressures are known through the entire network, the velocity, Reynolds number, shear rates and shear stresses can be calculated using fundamental fluid equations.

Alternatively, once the flow rates and pressure at every segment and junction are known, one can design a new network, where fluids travel through the system with predetermined velocities, shear rates, shear stresses and Reynolds number. The knowledge of rates of fluid flow, shear stresses and shear rates, in a particular vascular system can also be used to determine whether a particular vascular system is diseased without necessarily imaging the system.

In addition, a knowledge of the rates of fluid flow, the Reynolds number, the conductances, the resistance to flow, the shear stresses and shear rates, and the like, in a particular vascular system can also be used to predict defects in vascular systems in the eyes, lungs, heart and the like.

The digital representation of the vascular structure can then be used to determine terminal endpoints of the paths in the vascular structure as shown in the FIG. 4. Identification of endpoints can be used to segregate pathways in the vascular network visible in the retina and can serve as reference points for various calculations that can be generated based upon the vascular structure thereof. These calculations can provide values of the end to end distance of a particular branch of the vascular network, the end to end distance of a portion of the vascular structure; the radius of gyration of the one branch, a plurality of branches or of the entire vascular structure; the persistence length of a branch, or of a portion of the vascular structure, or of the entire vascular structure; the average length between branches; the average branch length; the average orientation of the branches with respect to each other; the tortuosity of a branch, a portion of the vascular structure, or of the entire vascular structure; or the like.

Figure 5:
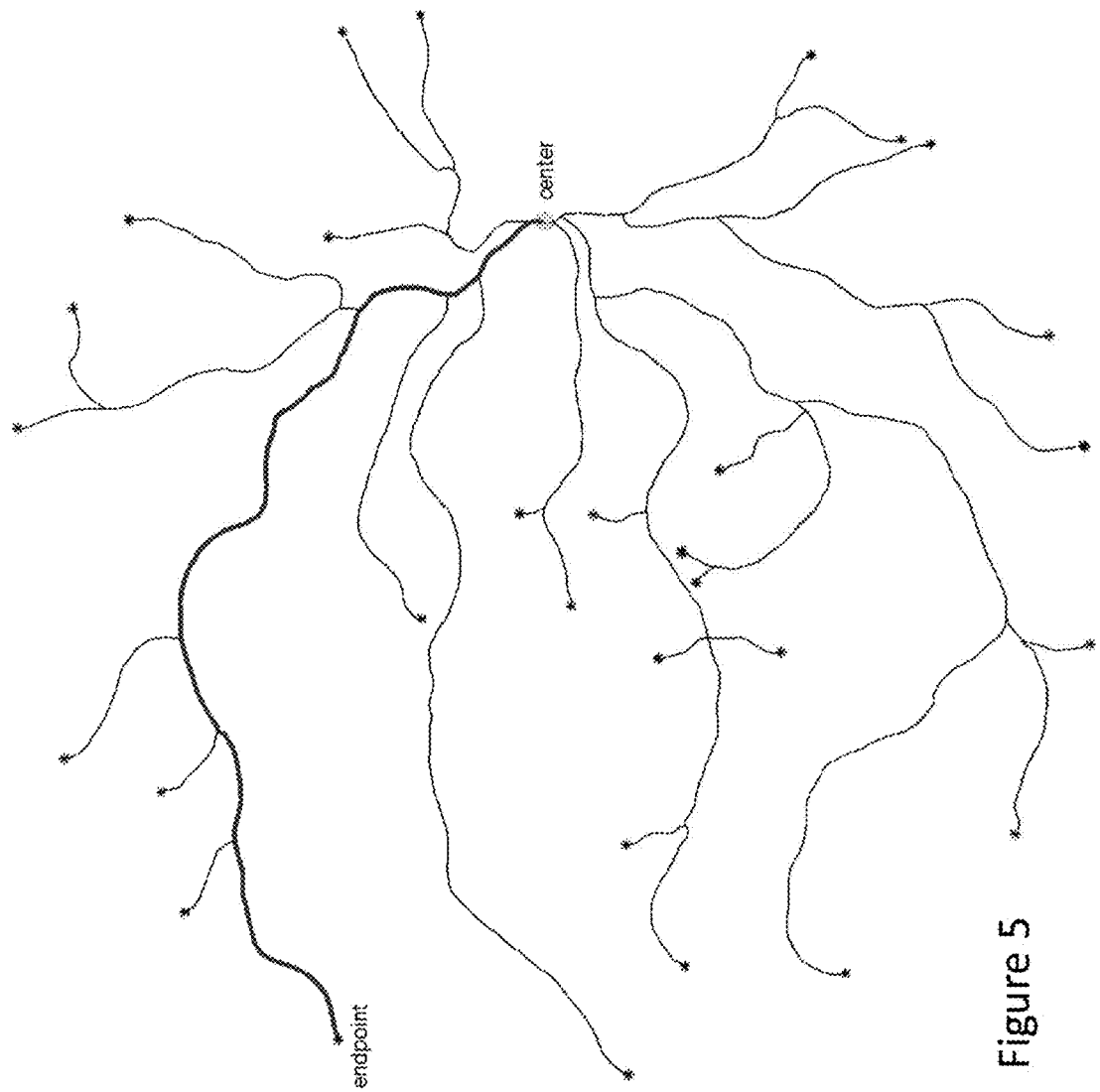
FIG. 5 is an image illustrating various paths in a vascular network of a subject retina according to various embodiments of the present disclosure.

Reference is now made to FIG. 5, which illustrates how once endpoints are identified in the binary representation of the vascular structure of the retina, a path from one or more of the endpoints can be traced to a path origin, and an effective length of a branch represented by the path can be determined from the binary representation. A branch path length is one measure of vascular network health. This process can be executed on the various endpoints detected in the binary representation of the vascular structure of the retina, and various branch path lengths calculated. In some embodiments, the process of detecting one or more branch path lengths is analogous to solving a maze. In one embodiment, a brute force method of maze solving can be employed, where the vascular network is randomly or pseudo-randomly traversed until all paths have been traversed.

Reference is now made to FIG. 6, which illustrates one method that can be employed to determine the path length of the various pathways in the vascular network of the retina. Various maze solving algorithms can be employed to determine a path between an endpoint and an origination point of a vascular network. For example, dead-end filling is one algorithm that can be employed to identify a path between an endpoint and the depicted center in the non-limiting example of FIG. 6. Such an algorithm can be employed on the various endpoints in the vascular network, and a path length calculated for each of the path. Each of the paths can correspond to a blood vessel and/or capillary that is visible in the retina. Accordingly, upon calculation of the path length associated with at least one path in the vascular network of the retina, various calculations can be made on the resultant data. In one embodiment, a mean path length as well as a standard deviation for at least a subset of the paths can be calculated. Other statistical calculations can be made on a set of data corresponding path lengths visible in a subject retina. These calculations can be compared to healthy patients to determine whether the data associated with a subject is correlated or within a particular statistical measure of a healthy patient. These calculations can also be compared to that of patients with various diagnoses and correlations can be made that may aid in the diagnosis of certain conditions.

Figure 7:
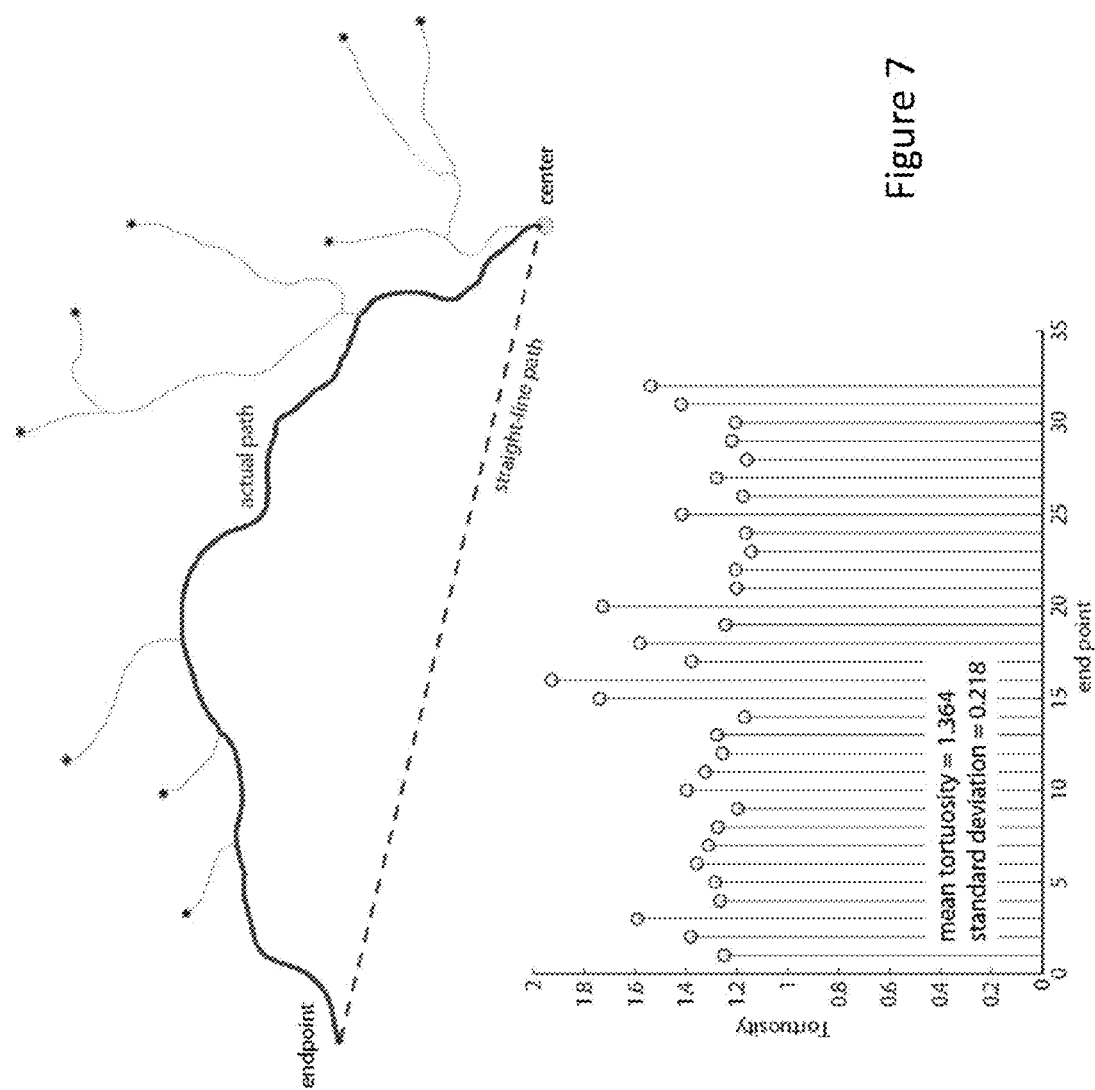
FIG. 7 illustrates an example of calculating a tortuosity measure associated with the various identified paths in a vascular network of a subject retina according to various embodiments of the present disclosure.

Reference is now made to FIG. 7, which illustrates an alternative and/or additional analysis that can be made on the various paths that are identified in the vascular network of the retina. As shown in the depicted illustration, an embodiment of the disclosure can calculate a tortuosity for at least one of the paths identified in the vascular network of a subject retina. Accordingly, an embodiment of the disclosure can calculate a tortuosity of various paths identified in a retina as well as various statistical measures with which the tortuosity of the subject retina can be compared to other measures associated with healthy patients and those diagnosed with certain conditions. Accordingly, a correlation can also be drawn with patients diagnosed with certain conditions in order to aid in the diagnoses of these conditions.

Figure 8:
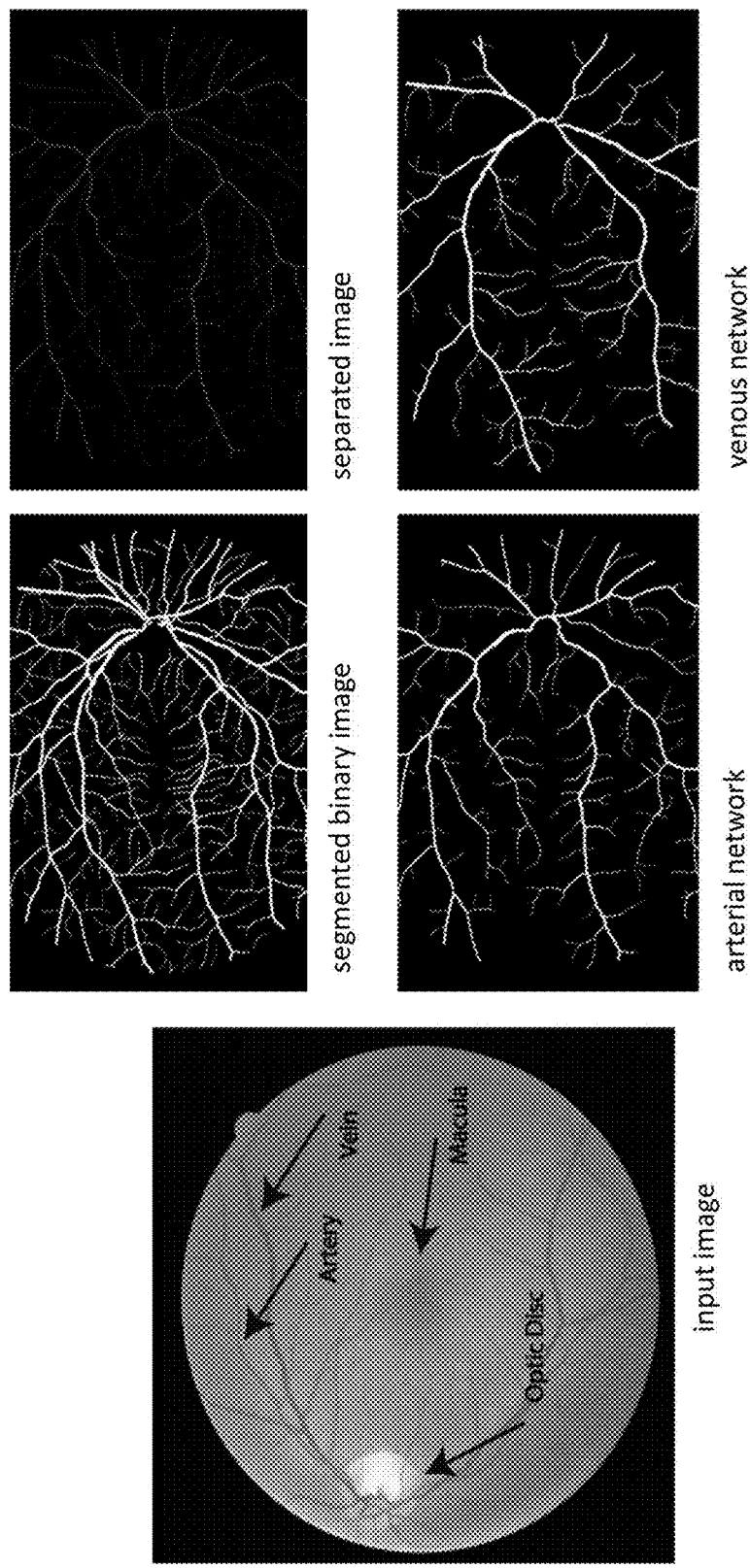
FIG. 8 illustrates an example of a constructal analysis according to various embodiments of the present disclosure.

With reference to the FIGS. 8 and 9, shown is an example of how constructal theory can be applied to an analysis of the exemplary subject retina. Generally speaking, constructal theory concerns the ability of a system to change its shape in order to accommodate flow efficiently. As shown in FIG. 9, a retinal image analysis of the vascular network of a subject retina can be conducted.

The methodology employed through constructal analysis involves understanding and determining the initial conditions, boundary conditions and operating constraints for optimizing the flow in an apparently random pathway, pattern or network. Vital sign data specific to each individual used for the initial and boundary conditions is also obtained. The image of the individual vasculature is also obtained. The medical image is then translated into a mathematical topological network to calculate the flow-related performance metrics (volumetric flow rates, velocities, vessel stresses, and the like.) at all nodes/segments of the network if the inlet pressure to the network is proportional to an applied pressure. The optimal network morphology that will yield the minimum global resistance to flow for the same individual operating constraints and input conditions is determined. The flow efficiency of a real network (e.g., a vascular network) can then be compared to the theoretical optimal-design network flow.

In one embodiment, the size, flow characteristics, volume, and other aspects of the various vessels in the vascular structure of the retina can be identified. Accordingly, by employing various fluid dynamics theories as well as constructal theory, an optimal flow angle associated with various junctions in the vascular network can be calculated. Therefore, an analysis of healthy patients as well as those diagnosed with certain conditions can yield various statistical measures with which an analysis of the subject retina can be correlated to aid in the diagnoses of certain conditions. It should be appreciated that an embodiment of the disclosure can calculate one or more measures associated with path length, tortuosity as well as a constructal analysis of the vascular network of the retina and, in combination, correlate one or more of these measures with healthy patients and/or those diagnosed with certain conditions.

Figure 10:
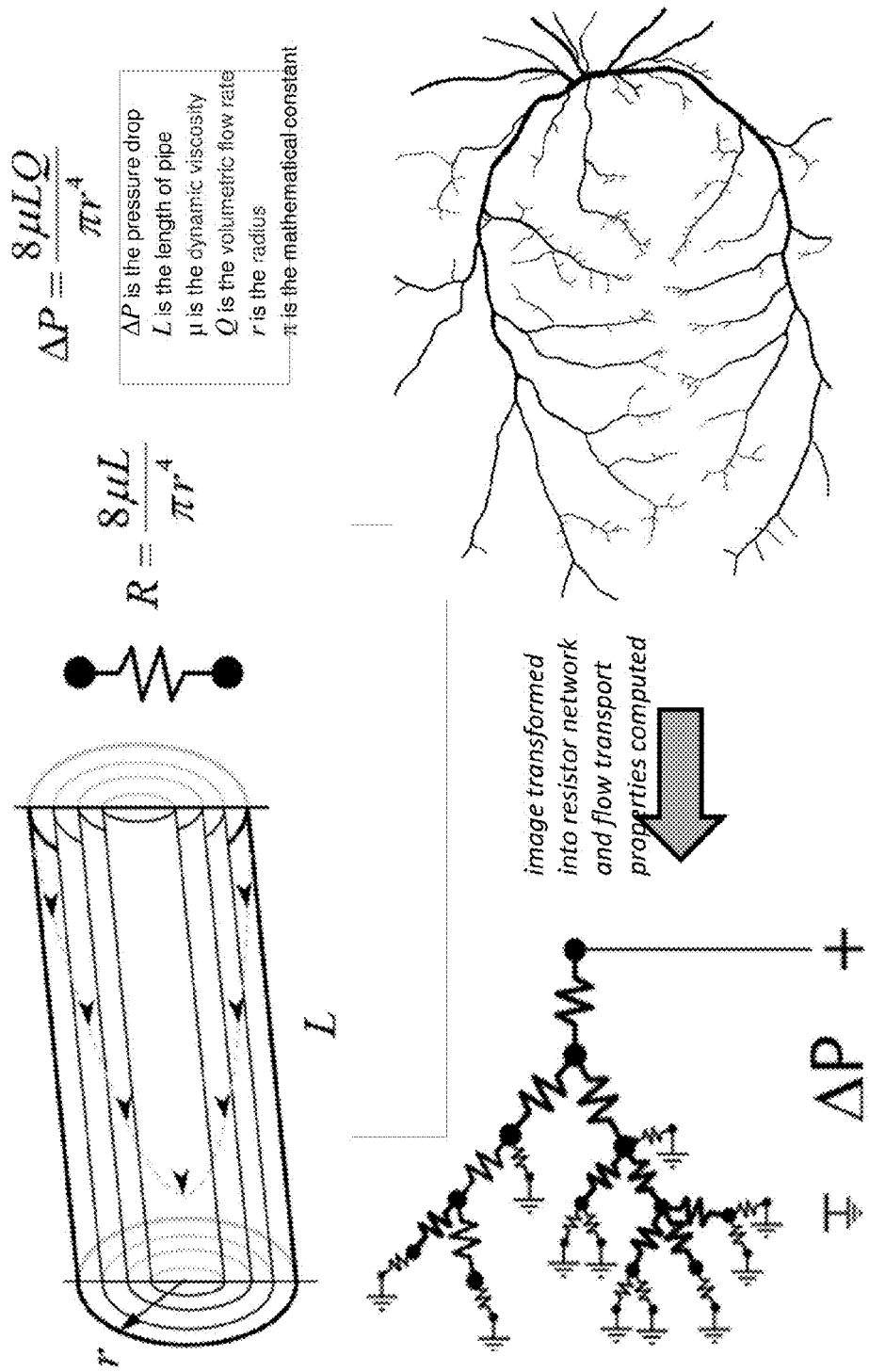
FIGS. 10 to 12 illustrate additional examples of a constructal analysis of a subject retina according to various embodiments of the present disclosure.
Figure 11:
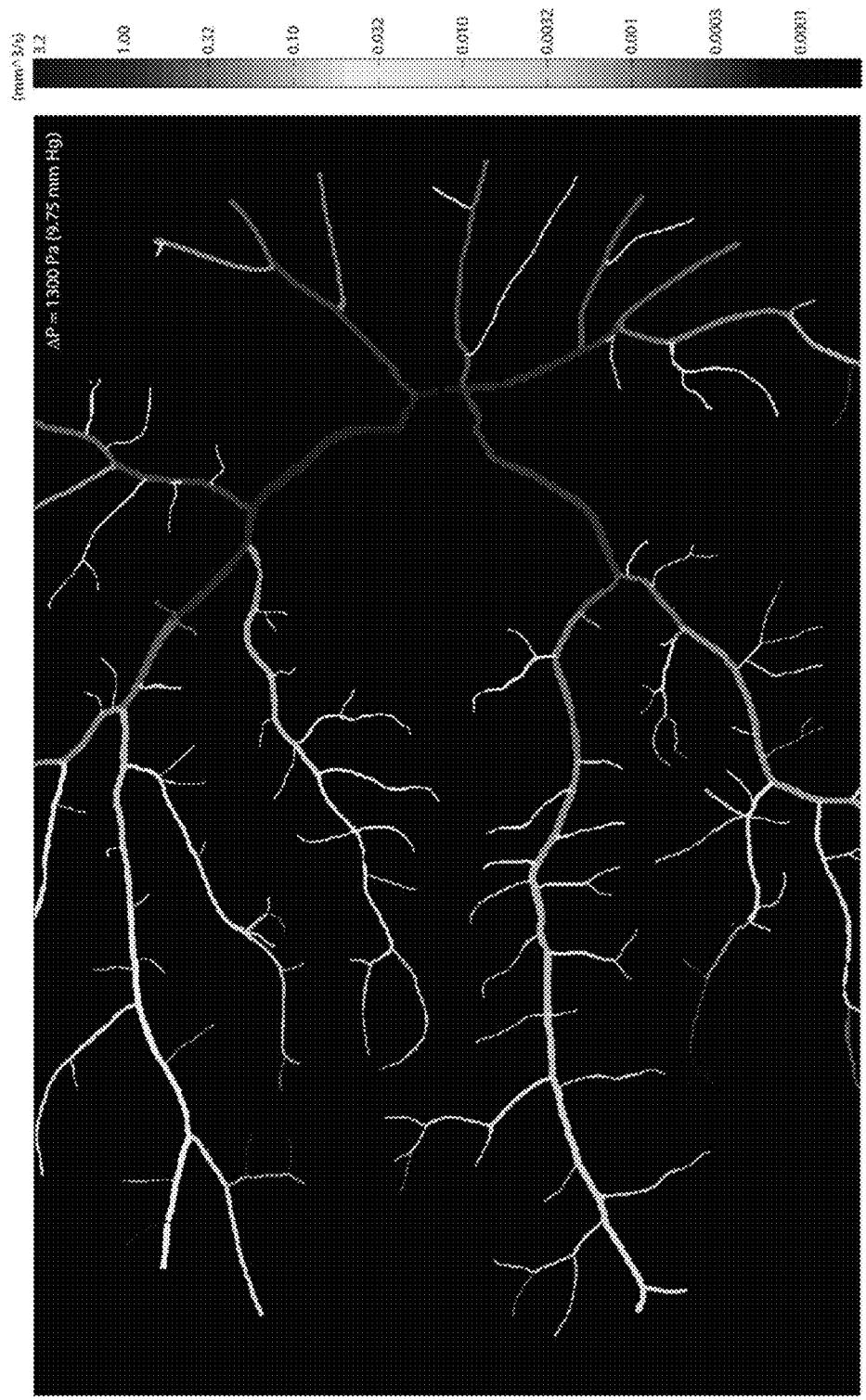
Figure 12:
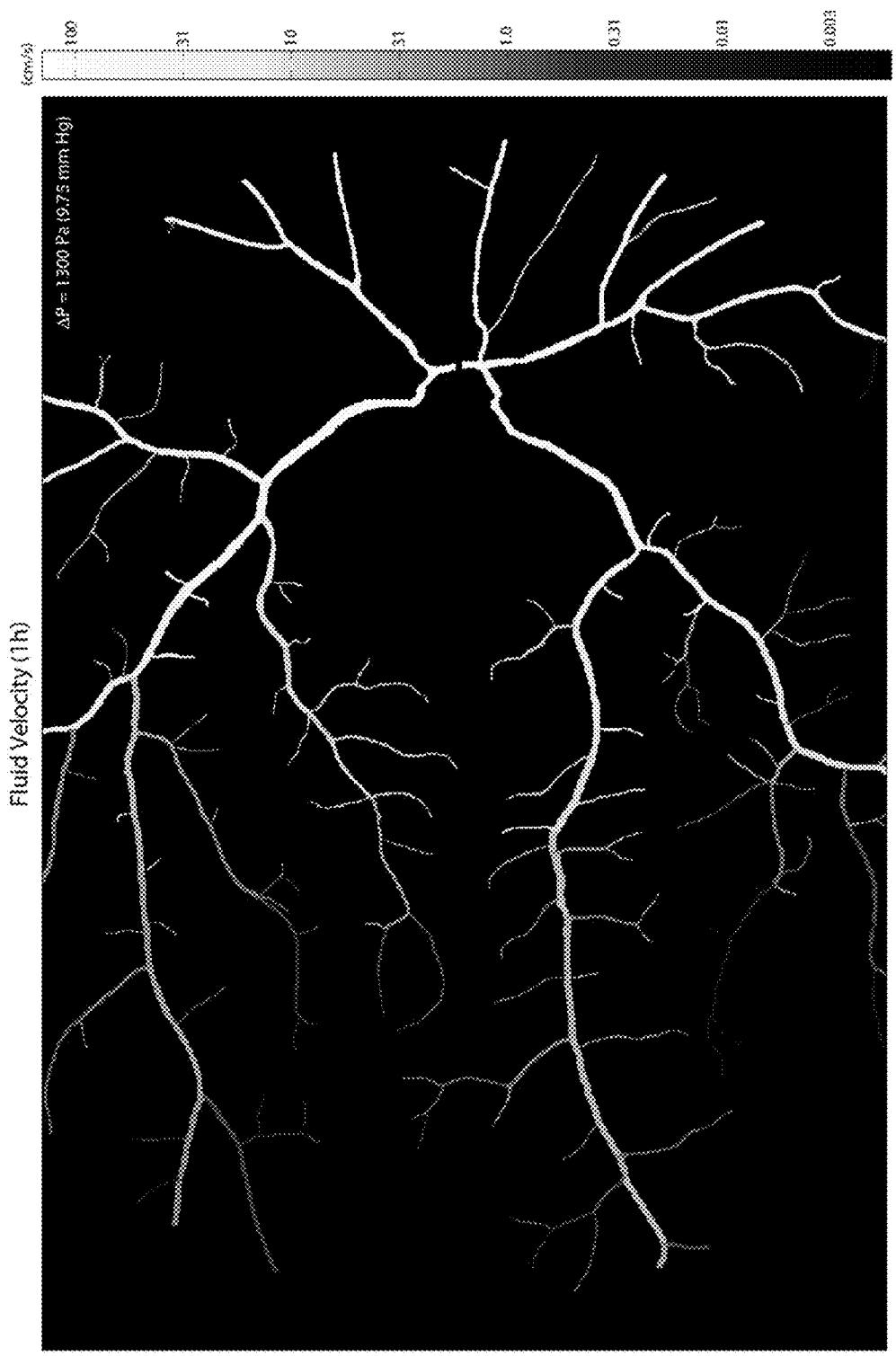

FIGS. 10 to 12 illustrate methods of describing a biological system such as a blood-flow through retinal vessels in terms of fluid network transport properties, which can be determined from vessel length as well as radius. As shown in the FIG. 10, the fluid transport properties of a retinal vessel network can be described in terms of an arterial resistor network. A retinal vessel network is computationally conceptualized as a resistor network and its fluid transport properties can be calculated based upon an image analysis of the retinal network.

For example, the vessel radius of each vessel in the skeletonized retinal network can be determined from an image analysis. The endpoints of each vessel are designated as a "ground" pressure, and resistances are determined from vessel length and radius, which assumes a steady, laminar flow of an ideal Newtonian fluid. As shown in the FIG. 11, a total volumetric flow as well as a volumetric flow at various points in the retinal network can therefore be determined. As shown in the FIG. 12, fluid velocities at various points in the retinal network can also be determined and mapped into imagery of the retinal network. Accordingly, these measures can be detected in a subject and compared with typical measures in patients with various diagnoses of certain conditions. Correlations can then be made that may aid in the diagnosis of certain conditions.

It should again be noted that while the examples discussed herein illustrate a constructal analysis of blood flow through the vascular network of a retina, the same analysis can be undertaken on any biological system within the body as well as with respect to any type of biological materials. For example, such a constructal analysis can be performed on a brain with respect to blood flow through the brain. As an additional example, the techniques discussed herein can also be applied to an analysis of one or more lungs of a patient with respect to blood flow and/or airflow through the one or more lungs. It can also be applied to the flow of electrons through nerves fibers. Other variations and permutations of a system and a material under analysis should be appreciated.

Embodiments of the present disclosure can be implemented as logic executed in one or more computing devices. A computing device according to the disclosure can include at least one processor and a memory, both of which are in electrical communication to a local interface. To this end, the computing device may comprise, for example, at least one server computer or like device. The local interface may comprise, for example, a data bus with an accompanying address/control bus or other bus structure as can be appreciated.

Stored in the memory are both data and several components that are executable by the processor. In particular, stored in the memory and executable by the processor is an application implementing logic according to the present disclosure as well as potentially other applications. It is understood that there may be other applications that are stored in the memory and are executable by the processors as can be appreciated. Where any component discussed herein is implemented in the form of software, any one of a number of programming languages may be employed such as, for example, C, C++, C#, Objective C, Java, Javascript, Perl, PHP, Visual Basic, Python, Ruby, Delphi, Flash, or other programming languages.

A number of software components are stored in the memory and are executable by the processor. In this respect, the term "executable" means a program file that is in a form that can ultimately be run by the processor. Examples of executable programs may be, for example, a compiled program that can be translated into machine code in a format that can be loaded into a random access portion of the memory and run by the processor, source code that may be expressed in proper format such as object code that is capable of being loaded into a random access portion of the memory and executed by the processor, or source code that may be interpreted by another executable program to generate instructions in a random access portion of the memory to be executed by the processor, etc. An executable program may be stored in any portion or component of the memory including, for example, random access memory (RAM), read-only memory (ROM), hard drive, solid-state drive, USB flash drive, memory card, optical disc such as compact disc (CD) or digital versatile disc (DVD), floppy disk, magnetic tape, or other memory components.

The memory is defined herein as including both volatile and nonvolatile memory and data storage components. Volatile components are those that do not retain data values upon loss of power. Nonvolatile components are those that retain data upon a loss of power. Thus, the memory may comprise, for example, random access memory (RAM), read-only memory (ROM), hard disk drives, solid-state drives, USB flash drives, memory cards accessed via a memory card reader, floppy disks accessed via an associated floppy disk drive, optical discs accessed via an optical disc drive, magnetic tapes accessed via an appropriate tape drive, and/or other memory components, or a combination of any two or more of these memory components. In addition, the RAM may comprise, for example, static random access memory (SRAM), dynamic random access memory (DRAM), or magnetic random access memory (MRAM) and other such devices. The ROM may comprise, for example, a programmable read-only memory (PROM), an erasable programmable read-only memory (EPROM), an electrically erasable programmable read-only memory (EEPROM), or other like memory device.

Also, the processor may represent multiple processors and the memory may represent multiple memories that operate in parallel processing circuits, respectively. In such a case, the local interface may be an appropriate network that facilitates communication between any two of the multiple processors, between any processor and any of the memories, or between any two of the memories, etc. The local interface may comprise additional systems designed to coordinate this communication, including, for example, performing load balancing. The processor may be of electrical or of some other available construction.

Although executable logic of an embodiment of the disclosure may be embodied in software or code executed by general purpose hardware as discussed above, as an alternative the same may also be embodied in dedicated hardware or a combination of software/general purpose hardware and dedicated hardware. If embodied in dedicated hardware, each can be implemented as a circuit or state machine that employs any one of or a combination of a number of technologies. These technologies may include, but are not limited to, discrete logic circuits having logic gates for implementing various logic functions upon an application of one or more data signals, application specific integrated circuits having appropriate logic gates, or other components, etc. Such technologies are generally well known by those skilled in the art and, consequently, are not described in detail herein.

Also, any logic or application according to an embodiment of the disclosure that comprises software or code can be embodied in any non-transitory computer-readable medium for use by or in connection with an instruction execution system such as, for example, a processor in a computer system or other system. In this sense, the logic may comprise, for example, statements including instructions and declarations that can be fetched from the computer-readable medium and executed by the instruction execution system. In the context of the present disclosure, a "computer-readable medium" can be any medium that can contain, store, or maintain the logic or application described herein for use by or in connection with the instruction execution system. The computer-readable medium can comprise any one of many physical media such as, for example, magnetic, optical, or semiconductor media. More specific examples of a suitable computer-readable medium would include, but are not limited to, magnetic tapes, magnetic floppy diskettes, magnetic hard drives, memory cards, solid-state drives, USB flash drives, or optical discs. Also, the computer-readable medium may be a random access memory (RAM) including, for example, static random access memory (SRAM) and dynamic random access memory (DRAM), or magnetic random access memory (MRAM). In addition, the computer-readable medium may be a read-only memory (ROM), a programmable read-only memory (PROM), an erasable programmable read-only memory (EPROM), an electrically erasable programmable read-only memory (EEPROM), or other type of memory device.

The data can be stored on the cloud and can be made accessible to specialists across the world. This will permit remote access of images and testing of patients in remote regions across the world. Storage of data on the cloud can be used to compare behavior or morphology in normal populations versus diseased populations and to aggregate such statistics in mass populations.

EXAMPLE

Example 1

This example was conducted to demonstrate the difference that can be detected between a normal healthy retina and a diabetic retina.

Figure 13:
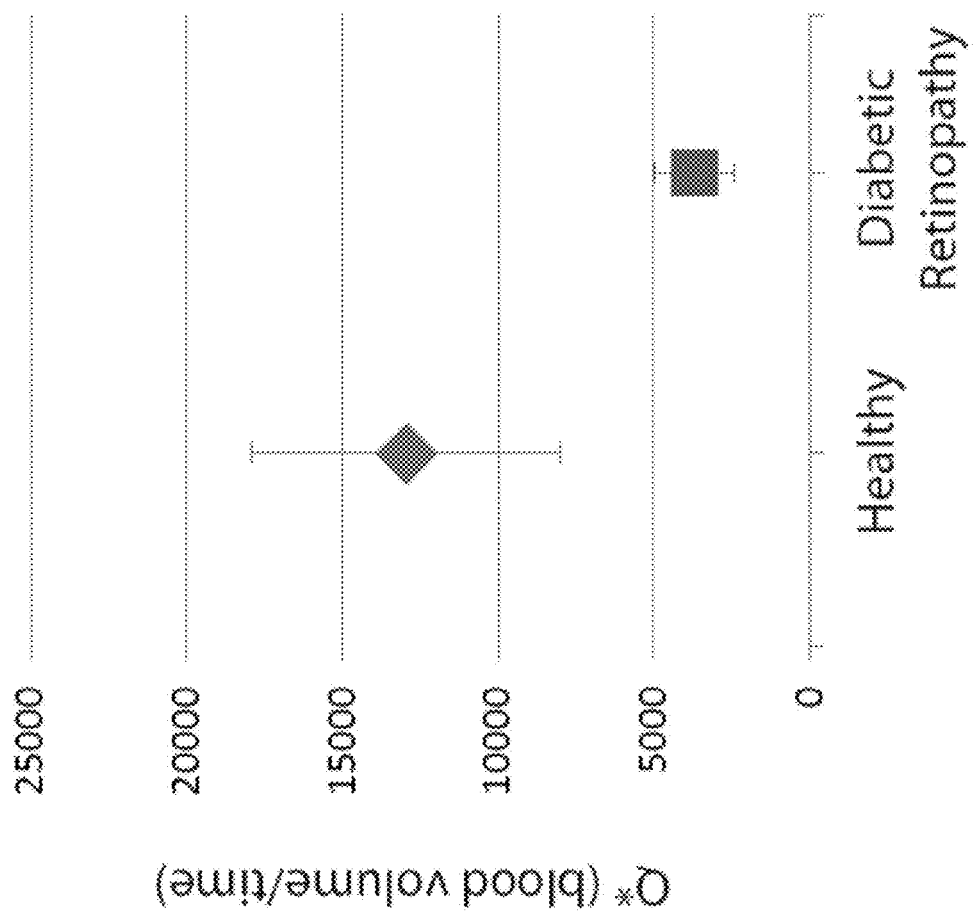
FIG. 13 is a graph depicting the difference between healthy blood vessels and blood vessels in the retina that are affected by the presence of diabetes.

A healthy retina and a diabetic retina were imaged and then subjected to constructal analysis as detailed above. The data is shown in the FIG. 13. FIG. 13 shows the volumetric blood flow results from a network-based analysis of the transport capability of health and diabetic eyes. The flow capacity of the network structure is determined by extracting individual vessel metrics (length, diameter, tortuosity, and the like) from the source image. The flow capacity is combined with a driving impetus (pressure difference for fluid networks) to determine the volume of blood that may pass through the network per unit time. In the FIG. 13, the diminution of blood vessels in the overall network caused by diabetes is manifested by reducing the amount of blood that may pass through the network in any amount of time. Compared with healthy networks (with larger capacity), a diagnostic determination can be made.

The method and the system disclosed above using constructal analysis may be used to study apparently random patterns, pathways, networks, or events. Examples of such apparently random pathways, patterns, networks, or events that can be characterized by this method are the growth of trees and plants, the growth and development of forests, the evolution and migration of certain types of species across the planet, the development and growth of blood vessels, the evolution and development of transportation networks across a state, country or continent, and the like.

The method and system can therefore be used for evaluation of automated fundus photograph analysis algorithms of a computer-assisted diagnostic system for grading diabetic retinopathy, therapeutic responses of anti-angiogenic drugs in choroidal neovascularization, evaluating optic neuritis along with degeneration of the retinal nerve fiber layer that is highly associated with multiple sclerosis, and ocular migraines associated with systemic vascular disease and high blood pressure.

The method and the system can also provide information about the neighborhood surrounding the apparently random patterns, pathways, networks, or events. This method can also be used to study a variety of different diseases affecting the different parts of the body. Examples are hypertension, chronic kidney failure, atherosclerosis (high cholesterol), pulmonary diseases such as emphysema, chronic bronchitis, asthma, chronic obstructive pulmonary disease, interstitial lung disease and pulmonary embolism, cardiovascular diseases such as myocardial infarction, aneurysms, transient ischemic attack, and brain diseases such as concussions, Alzheimer's disease and/or strokes.

It will be understood that, although the terms "first," "second," "third" etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, "a first element," "component," "region," "layer" or "section" discussed below could be termed a second element, component, region, layer or section without departing from the teachings herein.

The terminology used herein is for the purpose of describing particular embodiments only and is not intended to be limiting. As used herein, singular forms like "a," or "an" and "the" are intended to include the plural forms as well, unless the context clearly indicates otherwise. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

The term and/or is used herein to mean both "and" as well as "or". For example, "A and/or B" is construed to mean A, B or A and B.

The transition term "comprising" is inclusive of the transition terms "consisting essentially of" and "consisting of" and can be interchanged for "comprising".

While this disclosure describes exemplary embodiments, it will be understood by those skilled in the art that various changes can be made and equivalents can be substituted for elements thereof without departing from the scope of the disclosed embodiments. In addition, many modifications can be made to adapt a particular situation or material to the teachings of this disclosure without departing from the essential scope thereof. Therefore, it is intended that this disclosure not be limited to the particular embodiment disclosed as the best mode contemplated for carrying out this disclosure.

What is claimed is:

1. A system for performing a constructal analysis, the system comprising a processor and a memory to perform a method comprising:
    initiating capture of an image of a subject; where the subject comprises an apparent random pathway, pattern, or network; where the apparent random pathway, pattern or network comprises a flow field;
    initiating at least one image processing algorithm on the image;
    identifying at least one apparent random pathway, pattern, network, or one series of events in the image;
    identifying a center and at least one endpoint associated with the at least one apparent random pathway, pattern, network, or the event in the image;
    calculating a path length associated with the at least one apparent random pathway, pattern, network, or the event in the image;
    calculating at least one statistical measure associated the at least one apparent random pathway, pattern, network, or the one series of events in the image; where the statistical measure is calculated by constructal analysis;
    correlating the at least one statistical measure with a plurality of respective other statistical measures of at least one other apparent random pathway, pattern, network, or the one series of events in the subject or in another subject; where constructal analysis comprises determining initial conditions, boundary conditions and operating constraints for optimizing a flow in the apparently random pathway, pattern or network;
    translating the at least one apparent random pathway, pattern, network, or the one series of events in the image into a mathematical topological network;
    calculating flow-related performance metrics at all nodes of the at least one apparent random pathway, pattern, network, or the one series of events when an inlet pressure to the at least one apparent random pathway, pattern, network, or the one series of events is proportional to an applied pressure; and generating an optimal morphology design for the at least one apparent random pathway, pattern, network that will yield a minimum global resistance to flow for individual operating constraints and input conditions that the at least one apparent random pathway, pattern, network is subjected to.

2. The system of claim 1, where the subject is a vascular network of blood vessels in a living being, a network of capillaries in vegetation, a river that traverses the landscape, a polymer chain, a migratory pattern of a particular animal species, nerves in a nervous system, or electron or hole pathways in a conducting or semiconducting medium.

3. The system of claim 1, where the system is used to evaluate automated fundus photographic analysis algorithms of a computer-assisted diagnostic system for grading diabetic retinopathy, to evaluate therapeutic responses of anti-angiogenic drugs in choroidal neovascularization, to evaluate optic neuritis along with degeneration of the retinal nerve fiber layer that is highly associated with multiple sclerosis, to evaluate ocular migraines associated with systemic vascular disease and high blood pressure, to evaluate the condition of blood vessels and/or nerves when affected by hypertension, chronic kidney failure, atherosclerosis, pulmonary diseases such as emphysema, chronic bronchitis, asthma, chronic obstructive pulmonary disease, interstitial lung disease and pulmonary embolism, cardiovascular diseases, myocardial infarction, aneurysms, transient ischemic attack, brain diseases, concussions, Alzheimer's disease and/or strokes.

4. The system of claim 1, where the subject is a vascular network of blood vessels in a living being.

5. The system of claim 4, where the vascular network of blood vessels are present in a retina, a heart, a brain, breast, kidney, and/or a lung of a human being.

6. The system of claim 1, where the subject is a network of capillaries in vegetation.

7. The system of claim 1, where the image is obtained using magnetic resonance imaging, computed tomography, ultrasound, ultrasound thermography, opto-acoustics, infrared imaging, positron emission tomography, or xray imaging.

8. The system of claim 1, where the image is obtained using a camera or imaging device mounted on a satellite, an aircraft, a medical device, a fiber optic cable, a cell phone, or an observation tower.

9. The system of claim 1, where the image is further subjected to at least one of filtering, thresholding, digitization, and image and/or feature recognition.

10. The system of claim 1, where the at least one statistical measure is an end to end distance of the apparent random pathway, pattern, or network; an end to end distance of a portion of the apparent random pathway, pattern, or network; a radius of gyration of at least one branch or a plurality of branches of the apparent random pathway, pattern, or network; a persistence length of a branch or a plurality of branches of the apparent random pathway, pattern, or network; an average length between branches of the apparent random pathway, pattern, or network; an average branch length of the apparent random pathway, pattern, or network; an average orientation of the apparent random pathway, pattern, or network with respect to another apparent random pathway, pattern, or network; or the tortuosity of a branch or a plurality of branches of the apparent random pathway, pattern, or network.

11. A method for performing a constructal analysis of an apparent random pathway, pattern, network, or a series of events, comprising:

capturing at least one image of the apparent random pathway, pattern, network, or a series of events; where the apparent random pathway, pattern or network comprises a flow field;

initiating at least one image processing algorithm on the at least one image;

identifying in at least one computing device, at least one apparent random pathway, pattern, network, or event of the apparent random pathway, pattern, network, or the series of events;

identifying a center and at least one endpoint associated with the at least one apparent random pathway, pattern, network, or event, each of the at least one apparent random pathway, pattern, network, or event originating from the center of the apparent random pathway, pattern, network, or the series of events;

calculating, in the at least one computing device, a tortuosity measure associated with each of the at least one apparent random pathway, pattern, network, or event; where the calculating comprises determining initial conditions, boundary conditions and operating constraints for optimizing a flow in the apparently random pathway, pattern or network;

calculating, in the at least one computing device, at least one statistical measure associated with the apparent random pathway, pattern, network, or the series of events; and correlating the at least one statistical measure with a plurality of respective other statistical measures of at least one other apparent random pathway, pattern, network, or the series of events;

translating the at least one apparent random pathway, pattern, network, or series of events in the image into a mathematical topological network;

calculating flow-related performance metrics at all nodes of the at least one apparent random pathway, pattern, network, or series of events when an inlet pressure to the at least one apparent random pathway, pattern, network, or series of events is proportional to an applied pressure; and generating an optimal morphology design for the at least one apparent random pathway, pattern, network that will yield a minimum global resistance to flow for individual operating constraints and input conditions that the at least one apparent random pathway, pattern, network is subjected to.

12. The method of claim 11, where the capturing of the at least one image is accomplished via magnetic resonance imaging, computed tomography, ultrasound, ultrasound thermography, opto-acoustics, infrared imaging, positron emission tomography, or xray imaging.

13. The method of claim 11, where the capturing of the at least one image is accomplished via a camera or imaging device mounted on a satellite, an aircraft, a medical device, a fiber optic cable, a cell phone, or an observation tower.

14. The method of claim 11, where the apparent random pathway, pattern, network, or a series of events comprises a vascular network of blood vessels in a living being, a network of capillaries in vegetation, a river that traverses the landscape, a polymer chain, a migratory pattern of a particular animal species, or electron or hole pathways in a conducting or semiconducting medium.

15. The method of claim 11, where the method is used to evaluate automated fundus photographic analysis algorithms of a computer-assisted diagnostic system for grading diabetic retinopathy, to evaluate therapeutic responses of anti-angiogenic drugs in choroidal neovascularization, to evaluate optic neuritis along with degeneration of the retinal nerve fiber layer that is highly associated with multiple sclerosis, to evaluate ocular migraines associated with systemic vascular disease and high blood pressure, to evaluate the condition of blood vessels and/or nerves when affected by hypertension, chronic kidney failure, atherosclerosis, pulmonary diseases such as emphysema, chronic bronchitis, asthma, chronic obstructive pulmonary disease, interstitial lung disease and pulmonary embolism, cardiovascular diseases, myocardial infarction, aneurysms, transient ischemic attack, brain diseases, concussions, Alzheimer's disease and/or strokes.

16. The method of claim 11, where the apparent random pathway, pattern, network, or a series of events comprises a vascular network of blood vessels in a living being.

17. The method of claim 16, where the vascular network of blood vessels are present in a retina, a heart, a brain, breast, kidney, and/or a lung of a human being.

18. The method of claim 11, further comprising performing one of filtering, thresholding, digitization, and image and/or feature recognition on the image.

19. The method of claim 11, wherein the calculating the at least one statistical measure associated with the apparent random pathway, pattern, network, or the series of events is accomplished via a constructal analysis.

20. The method of claim 19, wherein the at least one statistical measure associated with the apparent random pathway, pattern, network, or the series of events provides information about the neighborhood of the apparent random pathway, pattern, network, or the series of events.

21. A method for performing a constructal analysis of a subject biological system, comprising the steps of:
   capturing at least one image of the subject biological system;
   initiating, in at least one computing device, at least one image processing algorithm on the at least one image;
   identifying at least one blood vessel in a vascular network of the subject biological system;
   identifying, in the at least one computing device, a plurality of junction angles associated with the at least one blood vessel in the vascular network of the subject biological system;
   calculating, in the at least one computing device, an optical flow measure associated with each of the at least one junction angle;
   calculating, in the at least one computing device, at least one statistical measure associated with a plurality of optimal flow angles associated with the subject biological system; where calculating the at least one statistical measure comprises determining initial conditions, boundary conditions and operating constraints for optimizing a flow in the vascular network;
   correlating the at least one statistical measure with a plurality of respective other statistical measures of at least one other patient;
   translating the vascular network in the image into a mathematical topological network;
   calculating flow-related performance metrics at all nodes of the vascular network in the image when an inlet pressure to the vascular network is proportional to an applied pressure; and
   generating an optimal morphology design for the vascular network that will yield a minimum global resistance to flow for individual operating constraints and input conditions that the vascular network is subjected to.

* * * * *